(12) United States Patent
Rose et al.

(10) Patent No.: US 8,062,642 B1
(45) Date of Patent: Nov. 22, 2011

(54) PRODUCTION OF PAPILLOMAVIRUS CAPSID PROTEIN AND VIRUS-LIKE PARTICLES

(75) Inventors: Robert Rose, Dansville, NY (US); William Bonnez, Rochester, NY (US); Richard Reichman, Pittsford, NY (US)

(73) Assignee: University of Rochester, Rochester, NY (US)

( * ) Notice: Subject to any disclaimer, the term of this patent is extended or adjusted under 35 U.S.C. 154(b) by 0 days.

(21) Appl. No.: 08/028,517

(22) Filed: Mar. 9, 1993

(51) Int. Cl.
*A61K 39/12* (2006.01)

(52) U.S. Cl. .................. 424/204.1; 435/69.1; 435/69.3; 530/300

(58) Field of Classification Search .................. 530/350, 530/826; 424/88, 89, 204.1, 185.1, 186.1; 435/69.3, 235.1, 236
See application file for complete search history.

(56) References Cited

U.S. PATENT DOCUMENTS

| | | | |
|---|---|---|---|
| 4,777,239 A | 10/1988 | Schoolnik et al. | |
| 4,870,023 A | 9/1989 | Fraser et al. | |
| 5,041,385 A | 8/1991 | Kingsman et al. | |
| 5,045,447 A | 9/1991 | Minson | |
| 5,057,411 A | 10/1991 | Lancaster et al. | |
| 5,071,757 A | 12/1991 | Kreider et al. | |
| 5,169,766 A | 12/1992 | Schuster et al. | |
| 5,346,811 A | 9/1994 | Galindo-Castrol | |
| 5,437,951 A * | 8/1995 | Lowy et al. ................ | 435/69.1 |
| 5,716,620 A | 2/1998 | Lowy et al. | |
| 5,744,142 A | 4/1998 | Lowy et al. | |
| 5,871,998 A | 2/1999 | Lowy et al. | |
| 5,985,610 A | 11/1999 | Lowy et al. | |
| 6,013,262 A | 1/2000 | Frazer et al. | |
| 6,066,324 A | 5/2000 | Gissmann et al. | |
| 6,261,765 B1 | 7/2001 | McCarthy et al. | |
| 6,361,778 B1 | 3/2002 | Gissmann et al. | |
| 6,599,508 B1 | 7/2003 | Gissmann et al. | |
| 6,613,557 B1 | 9/2003 | Frazer et al. | |
| 7,169,585 B2 | 1/2007 | Frazer et al. | |
| 7,220,419 B2 | 5/2007 | Lowy et al. | |
| 7,361,356 B2 | 4/2008 | Lowy et al. | |
| 7,416,732 B2 | 8/2008 | Gissmann et al. | |
| 7,476,389 B1 | 1/2009 | Frazer et al. | |
| 2009/0252761 A1 | 10/2009 | Frazer et al. | |

FOREIGN PATENT DOCUMENTS

| | | |
|---|---|---|
| EP | 0 343 783 A3 | 4/1989 |
| EP | 0 390 252 A3 | 3/1990 |
| WO | WO 94/00152 | 6/1992 |
| WO | WO 9210513 | 6/1992 |
| WO | WO 92/16636 A1 | 10/1992 |
| WO | WO 9216636 | 10/1992 |
| WO | WO 93/02184 | 2/1993 |
| WO | WO9302184 | 2/1993 |
| WO | WO 94/05792 | 3/1994 |

OTHER PUBLICATIONS

Ellis, R.W. "New technologies for making vaccines" In: Vaccines Plotkin and Mortimer Eds., W.B. Saunders Co. 1988, pp. 568-575.*
Rose, R.C et al. J. Virology 67(4): 1936-1944 (1993).*
Haginsec, M.E. et al. J. Virology 67(1): 315-322 (1993).*
Xi, S.Z. et al. J. Gen. Virology 72: 2981-2988 (1991).*
Zhou, J. et al. Virology 185: 251-257 (1991).*
Browne, H et al. J. Gen. Virol 69: 1263-1273, 1988.*
Kirnbauer et al. Journal of Virology 67:6929-6936, 1993.*
Kirnbauer et al. Journal of the National Cancer Institute 86:494-499, 1994.*
Kirnbauer, et al., Papillomavirus L1 major capsid protein self assemblies into virus-like particles that are highly immunogenic 1992, *Proc. Natl. Acad. Sci. USA*, vol. 89, pp. 12180-12184.
Karasuyama et al., "Establishment of Mouse Cell Lines Which Constitutively Secrete Large Quantities of Interleukin 2, 3, 4 or 5, Using Modified cDNA Expression Vectors," *Eur. J. Immunol.*, 18:97-104(1988).
Anisimová et al., "Presence and Type Specificity of Papillomavirus Antibodies Demonstrable by Immunoelectron Microscopy Tests in Samples from Patients with Warts," *J. Gen. Virol.* 71:419-22 (1990).
Baker et al., "Structures of Bovine and Human Papillomaviruses," *Biophys. J.* 60:1445-56 (1991).
Biberstein, "Immunization Therapy of Warts," *Arch. Dermatol. Syphilol.* 50:12-22 (1944).
Bonnez et al., "Antibody Response to Human Papillomavirus (HPV) Type 11 in Children with Juvenile-Onset Recurrent Respiratory Papillomatosis (RRP)," *Virology* 188:384-87 (1992).
Bonnez et al., "Antibody-Mediated Neutralization of Human Papillomavirus Type 11 (HPV-11) Infection in the Nude Mouse: Detection of HPV-11 mRNAs," *J. Infect. Dis.* 165:376-80 (1992).
Bonnez et al., "Evolution of the Antibody Response to Human Papillomavirus Type 11 (HPV-11) in Patients with Condyloma Acuminatum According to Treatment Response," *J. Med. Virol.* 39:340-44 (1993). Bonnez et al., "The PstI-XhoII Restriction Fragment of the HPV-6b L1 ORF Lacks Immunological Specificity as Determined by Sera from HPV6 Condyloma Acuminatum Patients and Controls," in [Papillomaviruses] 124 UCLA Symposia on Molecular and Cellular Biology: New Series 77-80 (1990).
Bonnez et al., "Use of Human Papillomavirus Type 11 Virons in an ELISA to Detect Specific Antibodies in Humans with Condylomata Acuminata," *J. Gen. Virol.* 72:1343-47 (1991).
Bowie et al., "Deciphering the Message in Protein Sequences: Tolerance to Amino Acid Substitutions," *Science* 247:1306-10 (1990).

(Continued)

*Primary Examiner* — Bo Peng
(74) *Attorney, Agent, or Firm* — LeClairRyan, a Professional Corporation; Michael L. Goldman

(57) ABSTRACT

The present invention is directed to a method of expressing the papillomavirus capsid protein coding sequence in a cell using an expression system under conditions facilitating expression of the protein in the cell.
In another aspect of the invention, it has been discovered that virus-like particle(s) (VLPs), fragment(s), capsomer(s) or portion(s) thereof are formed from the papillomavirus capsid protein. It was further discovered that the virus-like particle(s) comprises antigenic characteristics similar to those of native infectious papillomavirus particles.
In an embodiment of the invention, there is provided a method of expressing the L1 major capsid protein of human papillomavirus type-11 (HPV-11) in Sf-9 insect cells using the baculovirus expression system, and the production of HPV-11 virus-like particles.

44 Claims, 7 Drawing Sheets

OTHER PUBLICATIONS

Chan et al., "Phylogenetic Analysis of 48 Papillomavirus Types and 28 Subtypes and Variants: A Showcase for the Molecular Evolution of DNA Viruses," *J. Virol.* 66(10):5714-25 (1992).

Christensen & Kreider, "Antibody-Mediated Neutralization in Vivo of Infectious Papillomaviruses," *J. Virol.* 64(7):3151-56 (1990).

Christensen & Kreider, "Neutralization of CRPV Infectivity by Monoclonal Antibodies That Identify Conformational Epitopes on Intact Virions," *Virus Res.* 21:169-79 (1991).

Christensen et al., "Detection of Human Serum Antibodies That Neutralize Infectious Human Papillomavirus Type 11 Virions," *J. Gen. Virol.* 73:1261-67 (1992).

Christensen et al., "Monoclonal Antibody-Mediated Neutralization of Infectious Human Papillomavirus Type 11," *J. Virol.* 64(11):5678-81 (1990).

Cole & Danos, "Nucleotide Sequence and Comparative Analysis of the Human Papillomavirus Type 18 Genome: Phylogeny of Papillomaviruses and Repeated Structure of the E6 and E7 Gene Products," *J. Mol. Biol.* 193:599-608 (1987).

Cole & Mango, "cis-Acting Determinants of c-myc mRNA Stability," *Enzyme* 44:167-80 (1990).

Cornelissen et al., "Localization of Human Papillomavirus Type 16 DNA Using the Polymerase Chain Reaction in the Cervix Uteri of Women with Cervical Intraepithelial Neoplasia," *J. Gen. Virol.* 70:2555-62 (1989).

Crum & Levine, "Human Papillomavirus Infection and Cervical Neoplasia: New Perspectives," *Int'l J. Gynecol. Pathol.* 3:376-88 (1984).

Danos et al., "Papillomavirus Genomes: Sequences and Consequences," *J. Invest. Dermatol.* 83(1 Supp.):7s-11s (1984).

Dartmann et al., "The Nucleotide Sequence and Genome Organization of Human Papilloma Virus Type 11," *Virology* 151:124-30 (1986).

Doorbar & Gallimore, "Identification of Proteins Encoded by the L1 and L2 Open Reading Frames of Human Papillomavirus 1a," *J. Virol.* 61(9):2793-99 (1987).

Dürst et al., "A Papillomavrus DNA from a Cervical Carcinoma and Its Prevalence in Cancer Biopsy Samples from Different Geographic Regions," *Proc. Nat'l Acad. Sci. USA* 80:3812-15 (1983).

European Search Report, European Patent Application No. EP 05 07 5369 (Aug. 9, 2005).

Frazer, Slides Presented at the $10^{th}$ International Papillomavirus Workshop (Seattle, Washington, Jul. 20-26, 1991).

Ghim et al., "Comparison of Neutralization of BPV-1 Infection of C127 Cells and Bovine Fetal Skin Xenografts," *Int'l J. Cancer* 49:285-89 (1991).

Ghim et al., "HPV-1 L1 Protein Expressed in cos Cells Displays Conformational Epitopes Found on Intact Virions," *Virology* 190:548-52 (1992).

Gissmann et al., "Human Papilloma Viruses (HPV): Characterization of Four Different Isolates," *Virology* 76:569-80 (1977).

Gissmann et al., "Human Papillomaviruses and Cervical Cancer," *Cancer Cells* 5:275-80 (1987).

Hood et al., "Clarification and Retraction: Immunology," *Proc. Nat'l Acad. Sci. USA* 88:6899 (1991).

Howley, "Papillomavirinae and Their Replication," in 2 Fundamental Virology 743-68 (Bernard N. Fields and David M. Knipe eds., 2d ed. 1991).

International Preliminary Examination Report, International Patent Application No. PCT/US94/02443 (Jun. 13, 1995).

International Search Report, International Patent Application No. PCT/US94/02443 (Jun. 24, 1994).

Jenison et al., "Identification of Immunoreactive Antigens of Human Papillomavirus Type 6b by Using *Escherichia coli*-Expressed Fusion Proteins," *J. Virol.* 62(6):2115-23 (1988).

Kienzler et al., "Humoral and Cell-Mediated Immunity to Human Papillomavirus Type I (HPV-I) in Human Warts," *Br. J. Dermatol.* 108:665-72 (1983).

Klug & Finch, "Structure of Viruses of the Papilloma-Polyoma Type I. Human Wart Virus," *J. Mol. Biol.* 11:403-23 (1965).

Komly et al., "The L2 Open Reading Frame of Human Papillomavirus Type 1a Encodes a Minor Structural Protein Carrying Type-Specific Antigens," *J. Virol.* 60(2):813-16 (1986).

Koutsky et al., "Epidemiology of Genital Human Papillomavirus Infection," *Epidemiol. Rev.* 10:122-63 (1988).

Kreider et al., "Laboratory Production in Vivo of Infectious Human Papillomavirus Type 11," *J. Virol.* 61(2):590-93 (1987).

Kreider et al., "Morphological Transformation in Vivo of Human Uterine Cervix with Papillomavirus from Condylomata Acuminata," *Nature* 317:639-41 (1985).

Kumar et al., "Amino Acid Variations at a Single Residue in an Autoimmune Peptide Profoundly Affect Its Properties: T-Cell Activation, Major Histocompatibility Complex Binding, and Ability to Block Experimental Allergic Encephalomyelitis," *Proc. Nat'l Acad. Sci. USA* 87:1337-41 (1990).

Laemmli, "Cleavage of Structural Proteins During the Assembly of the Head of Bacteriophage T4," *Nature* 227:680-85 (1970).

Li et al., "Identification of the Human Papillomavirus Type 6b L1 Open Reading Frame Protein in Condylomas and Corresponding Antibodies in Human Sera," *J. Virol.* 61(9):2684-90 (1987).

Ludwik Gross, Oncogenic Viruses (3d ed. 1983) (Cover Page and Table of Contents only).

Malison et al., "Autogenous Vaccine Therapy for Condyloma Acuminatum: A Double-Blind Controlled Study," *Br. J Vener. Dis.* 58:62-65 (1982).

Max D. Summers & Gale E. Smith, A Manual of Methods for Baculovirus Vectors and Insect Cell Culture Procedures (Texas Agricultural Experiment Station, Bulletin No. 1555, May 1987).

McLean et al., "Production and Characterisation of a Monoclonal Antibody to Human Papillomavirus Type 16 Using Recombinant Vaccinia Virus," *J Clin. Pathol.* 43:488-92 (1990).

Nigel J. Dimmock, Neutralization of Animal Viruses (1993) (Cover Page and Table of Contents only).

Orth et al., "Characterization of a New Type of Human Papillomavirus That Causes Skin Warts," *J. Virol.* 24(1):108-20 (1977).

Parton, "Nucleotide Sequence of the HPV16 L1 Open Reading Frame," *Nucl. Acids Res.* 18(12):3631 (1990).

Patent Interference No. 104,773 (*Rose v. Frazer*), Declaration of Robert C. Rose, Ph.D. ¶¶ 172, 300 (Sep. 24, 2004).

Patent Interference No. 104,773 (*Rose v. Frazer*), Frazer Principal Brief for Case-in-Chief (Nov. 8, 2004).

Patent Interference No. 104,773 (*Rose v. Frazer*), Frazer Reply Brief for Case-in-Chief (Apr. 19, 2005).

Patent Interference No. 104,773 (*Rose v. Frazer*), Paper 278, Decision—Frazer Priority Date—Bd.R. 125(a) (Sep. 20, 2005).

Patent Interference No. 104,773 (*Rose v. Frazer*), Rose Opposition Brief on the Issue of Priority (Feb. 28, 2005).

Pfister & Zur Hausen, "Seroepidemiological Studies of Human Papilloma Virus (HPV-1) Infections," *Int'l J. Cancer* 21:161-65 (1978).

Powell et al., "Treatment of Condyloma Acuminata by Autogenous Vaccine," *South. Med. J.* 63:202-05 (1970).

Principles and Practice of Infectious Diseases (Gerald L. Mandell et al. eds., 3rd ed. 1990) (Table of Contents only).

Reichman & Bonnez, "Papillomaviruses," in Principles and Practice of Infectious Diseases 1191-200 (Gerald L. Mandell et al. eds., 3rd ed. 1990).

Rose et al., "Expression of the Full-Length Products of the Human Papillomavirus Type 6b (HPV-6b) and HPV-11 L2 Open Reading Frames by Recombinant Baculovirus, and Antigenic Comparisons with HPV-11 Whole Virus Particles," *J. Gen. Virol.* 71:2725-29 (1990).

Rose, Abstract, "Approaches to the Study of Humoral Immune Responses to Human Papillomavirus Infection Using Recombinant Baculoviruses," *MBI 501 Microbiology & Immunology Student Seminar*, Sep. 12, 1991.

Rose, Abstract, "Recombinant Baculovirus-Mediated Production of Non-Infectious Human Papillomavirus Type 11 (HPV-11) Virus-Like Particles (VLPs)," *MBI 501 Student Seminar Series*, Sep. 24, 1992.

Savant-Bhonsale & Cleveland, "Evidence for Instability of mRNAs Containing AUUUA Motifs Mediated Through Translation-Dependent Assembly of a >20S Degradation Complex," *Genes Develop.* 6:1927-39 (1992).

Seedorf et al., "Human Papillomavirus Type 16 DNA Sequence," *Virology* 145:181-85 (1985).

Shaw & Kamen, "A Conserved AU Sequence from the 3' Untranslated Region of GM-CSF mRNA Mediates Selective mRNA Degradation," *Cell* 46:659-67 (1986).

Shyu et al., "Two Distinct Destabilizing Elements in the *c-fos* Message Trigger Deadenylation as a First Step in Rapid mRNA Decay," *Genes Develop.* 5:221-31 (1991).

Stanley & Luzio, "Construction of a New Family of High Efficiency Bacterial Expression Vectors: Identification of cDNA Clones Coding for Human Liver Proteins," *EMBO J.* 3(6):1429-34 (1984).

Steele & Gallimore, "Humoral Assays of Human Sera to Disrupted and Nondisrupted Epitopes of Human Papillomavirus Type 1," *Virology* 174:388-98 (1990).

Storey et al., "Lack of Immortalizing Activity of a Human Papillomavirus Type 16 Variant DNA with a Mutation in the E2 Gene Isolated from Normal Human Cervical Keratinocytes," *Oncogene* 7:459-65 (1992).

Stoscheck, "Quantitation of Protein," in [Guide to Protein Purification] 182 Methods in Enzymology 50-68 (Murray P. Deutscher ed., 1990).

Strike et al., "Expression in *Escherichia coli* of Seven DNA Fragments Comprising the Complete L1 and L2 Open Reading Frames of Human Papillomavirus Type 6b and Localization of the 'Common Antigen' Region," *J. Gen. Virol.* 70:543-55 (1989).

Supplementary European Search Report, European Patent Application No. EP 94 91 2186 (Apr. 11, 1996).

Viac et al., "Incidence of Antibodies to Human Papillomavirus Type 1 in Patients with *Cutaneous* and *Mucosal* Papillomas," *J. Med. Virol.* 32:18-21 (1990).

Viruses and Cancer (P.W.J. Rigby & N. M. Wilkie eds., 1985) (Table of Contents only).

Written Opinion, International Patent Application No. PCT/US94/02443 (Jan. 30, 1995).

Zhou et al., "Definition of Linear Antigenic Regions of the HPV16 L1 Capsid Protein Using Synthetic Virion-Like Particles," *Virology* 189:592-99 (1992).

Zhou et al., "Synthesis and Assembly of Infectious Bovine Papillomavirus Particles in Vitro," *J. Gen. Virol.* 74:763-68 (1993).

Zur Hausen, "Genital Papillomavirus Infections," in Viruses and Cancer 83-90 (P.W.J. Rigby & N.M. Wilkie eds., 1985).

Amendment dated Sep. 4, 2007, as filed in U.S. Appl. No. 08/216,506 to Schlegel et al.

Office Action dated Mar. 18, 2009, as entered in U.S. Appl. No. 08/216,506 to Schlegel et al.

Carter, J.J., et al., "Expression of Human Papillomavirus Proteins in Yeast *Saccharomyces cerevisiae*," *Virology* 182:513-21 (1991).

\* cited by examiner

SEQUENCE LISTING (1) GENERAL INFORMATION:

(iii) NUMBER OF SEQUENCES: 2

(2) INFORMATION FOR SEQ ID NO:1:

(i) SEQUENCE CHARACTERISTICS:
       (A) LENGTH: 24 base pairs
       (B) TYPE: nucleic acid
       (C) STRANDEDNESS: single
       (D) TOPOLOGY: linear (ii) MOLECULE TYPE: cDNA (xi) SEQUENCE DESCRIPTION: SEQ ID NO:1:

CGCAGATCTA TGTGGCGGCC TAGC                                    24

(2) INFORMATION FOR SEQ ID NO:2:

(i) SEQUENCE CHARACTERISTICS:
       (A) LENGTH: 30 base pairs
       (B) TYPE: nucleic acid
       (C) STRANDEDNESS: single
       (D) TOPOLOGY: linear (ii) MOLECULE TYPE: cDNA (xi) SEQUENCE DESCRIPTION: SEQ ID NO:2:

CATATGAATT CCCACAACAC ACTGACACAC                              30

PRODUCTION OF PAPILLOMAVIRUS CAPSID PROTEIN AND VIRUS-LIKE PARTICLES

FIELD OF THE INVENTION

The present invention relates generally to papillomavirus (PV). More particularly, the invention relates to a method of expressing the human papillomavirus (HPV) capsid protein coding sequence using the baculovirus expression system, production of HPV virus-like particles (VLPs) and use of these VLPs in production of antibodies which recognize epitopes on HPV, and for HPV vaccine development, and for development of serologic tests for the detection of HPV infection.

BACKGROUND OF THE INVENTION

The family Papovaviridae constitutes a group of DNA viruses that induce both lytic infections and either benign or malignant tumors. Structurally, all are naked icosahedral virions with 72 capsomeres and contain double-stranded circular DNA. Viruses included in the family are: (1) human and animal papillomaviruses, (2) mouse polyomavirus, (3) simian vacuolating virus, and (4) human viruses BK and JC.

Human papillomaviruses (HPV) infect cutaneous, genital, oral, and respiratory epithelia in a tissue-specific manner. Infection with HPV has been associated closely with the development of both benign lesions and malignancies (Reichman et al., Papillomaviruses, 1990, pp. 1191-1200; and Mandell et al., Principles and Practice of Infectious Diseases, 3rd ed., Churchill Livingstone, New York, N.Y.). For example, HPV type 1 (HPV-1) is present in plantar warts, HPV types 6 or 11 (HPV-6 or HPV-11) in condylomata acuminata (anogenital warts), while HPV types 16 or 18 (HPV-16 or HPV-18) are common in premalignant and malignant lesions of the cervical squamous epithelium (See: Crum et al., Human papillomavirus infection and cervical neoplasia: New perspectives, 1984, *Int. J. Gynecol. Pathol.*, vol. 3, pp. 376-388; zur Hausen, Genital papillomavirus Infections, 1985, pp. 83-90; Rigby et al., Viruses and Cancer, Cambridge University Press, Cambridge, UK; and Koutsky et al., Epidemiology of genital human papillomavirus infection, 1988, *Epidemiol. Rev.*, vol. 10, pp. 122-163).

However, difficulties in propagating HPV in vitro has led to the development of alternative approaches to antigen production for immunologic studies. For example, Bonnez et al., The PstI-XhoII restriction fragment of the HPV-6b L1 ORF lacks immunological specificity as determined by sera from HPV 6 condyloma acuminatum patients and controls, 1990, *UCLA Symp. Mol. Cell. Biol.*, New Series, vol. 124, pp. 77-80; Jenison et g., Identification of immunoreactive antigens of human papillomavirus type 6b by using *Escherichia coli*-expressed fusion proteins, 1988, *J. Virol.*, vol. 62, pp. 2115-2123; Li et al., Identification of the human papillomavirus type 6b L1 open reading frame protein in condylomas and corresponding antibodies in human sera, 1987, *J. Virol.*, vol. 61, pp. 2684-2690; Steele et al., Humoral assays of human sera to disrupted and nondisrupted epitopes of human papillomavirus type 1, 1990, *Virology*, vol. 174, pp. 388-398; and Strike et al., Expression in *Escherichia coli* of seven DNA segments comprising the complete L1 and L2 open reading frames of human papillomavirus type 6b and the location of the "common antigen", 1989, *J. Gen. Virol.*, vol. 70, pp. 543-555, have expressed recombinant capsid protein coding sequences in prokaryotic systems, and used them in Western blot analyses of sera obtained from individuals with HPV infection of the genital tract. Results from these studies have suggested that antibodies to denatured, i.e. linear, epitopes of HPV capsid proteins can be detected in the sera of some infected individuals.

Whole virus particles have also been used to detect antibodies in human sera, including antibodies directed against conformational epitopes. These studies have been difficult to conduct because most naturally occurring HPV-induced lesions produce few particles. Whole virus particles can be obtained, however, in amounts sufficient to conduct immunologic assays from HPV type 1-induced plantar warts (Kienzler et al., Humoral and cell-mediated immunity to human papillomavirus type 1 (HPV-1) in human warts, 1983, *Br. J. Dermatol.*, vol. 108, pp. 65-672; Pfister et al., Seroepidemiological studies of human papilloma virus (HPV-1) infections, 1978, *Int. J. Cancer*, vol. 21, pp. 161-165; and Steele et al., 1990, Humoral assays of human sera to disrupted and non-disrupted epitopes of human papillomavirus type 1, 1990, *Virology*, vol. 174, pp. 388-398) and experimentally-induced HPV-11 athymic mouse xenographs (Kreider et al., Laboratory production in vivo of infectious human papillomavirus type 11, 1987, *J. Virol.*, vol. 61, pp. 590-593; and Kreider et al., Morphological transformation in vivo of human uterine cervix with papillomavirus from condylomata acuminata, 1985, *Nature*, vol. 317, pp. 639-641). More particularly, U.S. Pat. No. 5,071,757 to Kreider et al., discloses a method of propagating infectious HPV-11 virions in the laboratory using an athymic mouse xenograph model system. Although this system is capable of producing quantities of infectious virus that could be used for the development of a serologic test for genital HPV infection, this system is very expensive and cumbersome. Furthermore, only one genital HPV type has so far been propagated in this system, thus, limiting its usefulness. In addition, the infectious virus produced using this system represents a biohazard and, therefore, would be difficult to use in a vaccine formulation.

Zhou et al., in "Expression of vaccinia recombinant HPV 16 L1 and L2 ORF proteins in epithelial cells is sufficient for assembly of HPV virion-like particles", 1992, *Virology*, vol. 185, pp. 251-257, have reported the formation of HPV-16 virus-like particles in CV-1 cell nuclei following infection with a vaccinia virus HPV-16 L1/L2 double recombinant expression vector. However, the authors were not able to produce VLPs with a vector expressing L1 alone. Furthermore, the VLPs produced lacked a well-defined symmetry, and were more variable in size and smaller, only about 35-40 nm in diameter than either HPV virions (55 nm) or the VLPs of the present invention (baculovirus produced HPV-11 VLPs, about 50 nm in diameter).

U.S. Pat. No. 5,045,447, to Minson, discloses a method of screening hybridoma culture supernatants for monoclonal antibodies with desired specificities. Minson's method is exemplified by the production of antibodies to the L1 protein of human papillomavirus type 16 (HPV-16) using this protein as the target antigen in mice. However, Minson fails to disclose the expression of the L1 protein or production of HPV virus-like particles (VLPs).

U.S. Pat. No. 4,777,239, to Schoolnik et al., discloses short peptide sequences derived from several of the papillomavirus early region open reading frames which elicit type-specific antibodies to papillomavirus. However, the inventors fail to disclose any sequences directed to the major late open reading frame, L1.

U.S. Pat. No. 5,057,411, to Lancaster et al., discloses a polynucleotide sequence of about 30 nucleotides of the papillomavirus L1 capsid protein open reading frame that the inventors contend encode a papillomavirus type-specific epitope. However, the inventors do not disclose infected animals that produced antibodies which recognize this sequence. Instead, they synthesized a bovine papillomavirus type 1 (BPV-1) version of the sequence (a 10 amino acid peptide, or decapeptide), then immunized rabbits and tested the antiserum's ability to react with either BPV-1 or BPV-2 induced fibropapilloma tissue. The peptide antiserum only reacted with BPV-1 and not BPV-2 tissue. The inventors then concluded that the peptide contained an antigenic determinant that was type-specific, and therefore, all papillomavirus L1 coding sequences contain a type-specific epitope at this locus. This is theoretical speculation on the part of the inventors, who give no supporting data for this hypothesis. In addition, the amino acid sequences disclosed (10 amino acids) are generally thought not to be capable of adopting higher order antigenic structures, i.e., conformational epitopes that possess a three-dimensional structure such as those produced by the method described herein.

Another problem associated with papillomavirus infections is the need for alternative therapeutic and prophylactic modalities. One such modality which has received little recent study, would be papillomavirus vaccines. In 1944, Biberstein treated condyloma acuminatum patients with an autogenous vaccine derived from the patients' warts (Biberstein, Immunization therapy of warts, *Arch. Dermatol Syphilol*, 1944, vol. 50, pp. 12-22). Thereafter, Powell et al., developed the technique typically used today for preparing autogenous wart vaccines for the treatment of condyloma acuminatum (Powell et al., Treatment of condylomata acuminata by autogenous vaccine, 1970, *South Med. J.*, vol. 63, pp. 202-205). Only one double-blind, placebo-controlled study has attempted to evaluate the efficacy of the autogenous vaccine (Malison et al., Autogenous vaccine therapy for condyloma acuminatum: A double-blind controlled study, 1982, *Br. J. Vener. Dis.*, vol. 58, pp. 62-65). The authors concluded that autogenous vaccination was not effective in the treatment of condylomata acuminata, although this interpretation may be erroneous. The small number of patients studied precluded drawing valid negative conclusions. In any event, autogenous vaccines, as presently described, have several disadvantages. First, the patient needs to have relatively large warts (2 g to 5 g) in order to prepare the vaccine. Secondly, the practitioner needs access to laboratory equipment and expertise each time a new patient is to be treated. Thus, vaccine preparation is very expensive, tedious, and in cases involving relatively small lesion mass, not possible.

Unfortunately, traditional methods of virus propagation have not yet been adapted to the study of papillomaviruses, and the alternative methods previously described fail to produce infectious virions in any significant amounts for immunologic studies. Also, in vivo propagation of HPV-11 in the athymic mouse system is not very practical because it is expensive, labor intensive and currently limited to HPV-11. Consequently, an alternative method of producing epitopes of HPV capsid for use in immunologic studies and vaccine production is needed.

SUMMARY OF THE INVENTION

The present invention is directed to a method of expressing the capsid protein coding sequence of papillomavirus (PV) in a cell, comprising transfecting the cell with an expression vector containing the papillomavirus capsid protein coding sequence under conditions facilitating expression of the protein in the cell.

In another aspect of the invention, there is provided a virus-like particle(s) (VLPs), fragment(s), capsomer(s) or portion(s) thereof, formed from papillomavirus capsid protein. It has been discovered that the virus-like particle(s) comprises antigenic characteristic(s) similar to those of native infectious papillomavirus particles.

In a preferred embodiment of the invention, there is provided a method of expressing the L1 capsid protein coding sequence of human papillomavirus type-11 (HPV-11) in Sf-9 insect cells using the baculovirus expression system. The HPV-11 coding sequence was cloned using standard techniques in the art into a baculovirus transfer vector. The resulting baculovirus transfer vector was used to co-transfect Sf-9 insect cells with *Autographa californica* nuclear polyhedrosis virus (AcNPV) forming a recombinant baculovirus (Ac11L1) which was recovered. Sf-9 insect cells were thereafter infected with Ac11L1 under conditions facilitating expression of the protein in the cells. It was discovered that the L1 protein formed virus-like particles (VLPs). VLPs were identified by electron microscopy of negatively-stained sucrose band fractions obtained from Sf-9 cells infected with the Ac11L1 recombinant baculovirus. It was further discovered that the VLPs possessed immunological and morphological characteristics similar to those of native HPV-11 virions, as defined by rabbit antisera.

Virus-like particle(s) produced in accordance with the invention, can be used in diagnostic assays, can play a role in the identification and characterization of an HPV cell receptor, and can be used for vaccine development (both therapeutic and prophylactic). It is understood that the method of the invention as described herein for production of HPV-11, HPV-6 and HPV-16 VLPs, can be used to produce similar immunologic reagents from other animal and/or human papillomaviruses. In addition, VLPs produced in accordance with the invention will provide abundant reagents with which to carry out immunologic studies of papillomaviruses and for developing vaccines against papillomaviruses.

DETAILED DESCRIPTION OF THE INVENTION

Figure 1:
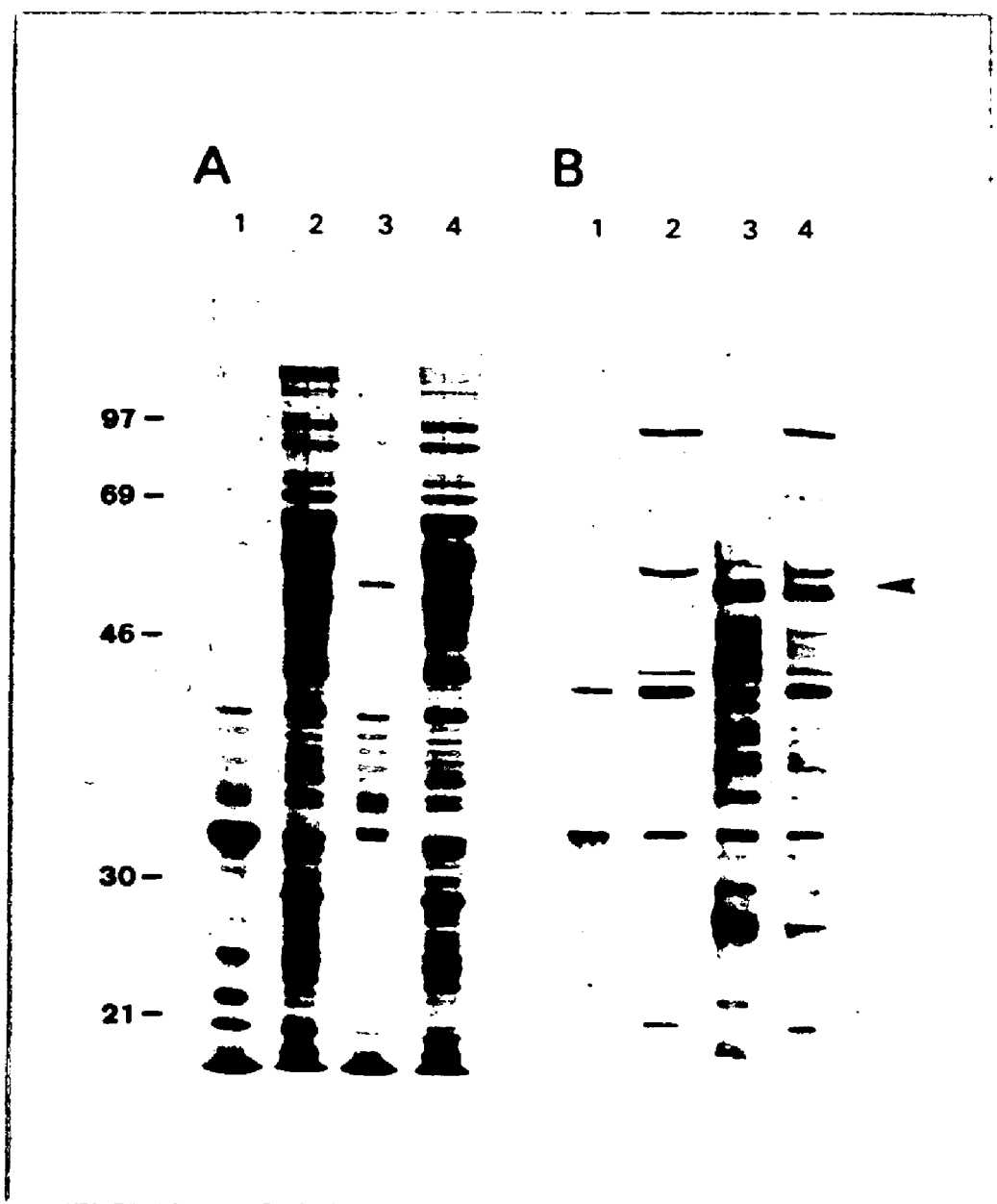
FIG. 1A shows Coomassie-blue stained SDS polyacrylamide gel of wild-type AcNPV and recombinant Ac11L1-infected Sf-9 cell lysates.
FIG. 1B shows a Western blot of wild-type AcNPV and recombinant Ac11L1-infected Sf-9 cell lysates probed with rabbit polyclonal antiserum specific for the HPV L1 common epitope.

The present invention is directed to a method of expressing the papillomavirus capsid protein coding sequence in a cell using the baculovirus expression system under conditions facilitating expression of the protein in the cell. In another aspect of the invention, it has been discovered that virus-like particle(s) (VLPs), fragment(s), capsomer(s) or portion(s) thereof are formed from the papillomavirus capsid protein. It was further discovered that the virus-like particle(s) comprises antigenic characterics similar to those of native infectious papillomavirus particles.

As used herein, "virus-like particle(s) (VLPs)" refer to a virus-like particle(s), fragment(s), capsomer(s) or portion(s) thereof produced from the capsid protein coding sequence of papillomavirus and comprising antigenic characteristic(s) similar to those of infectious papillomavirus particles. As used herein, "antigenic characteristic(s)" refers to (1) the ability of the virus-like particle(s) to cross-react with wild-type particles (native infectious virus particles) as determined by antisera generated in animals and/or humans by immunization with either VLPs or infectious virus; and/or (2) the ability to recognize or detect antibodies in human sera from persons known to be infected with homologous virus.

As used herein, "L1 protein coding sequence" or "L1 capsid protein coding sequence" or "L1 coding sequence" refers to the open reading frame which codes for the L1 protein in papillomavirus. When expressed, the L1 protein coding sequence produces a protein, or protein complex, or aggregate, which possesses immunological and morphological characteristics similar to those of native papillomavirus virions. The L1 coding sequence used in the invention can be isolated and purified from papillomavirus genomic DNA or synthesized using standard genetic engineering techniques.

As used herein, the term "transfecting" refers to any means for introducing a virus, plasmid or vector into a cell. Examples of such means include infection, calcium phosphate precipitation and electroporation.

In a preferred embodiment of the invention, there is provided a method of expressing the coding sequence for the L1 capsid protein of human papillomavirus type-11 (HPV-11), human papillomavirus type-6 (HPV-6), or human papillomavirus type-16 (HPV-16) in Sf-9 insect cells using the baculovirus expression system. It is understood that the capsid protein coding sequences of these HPV types are used for purposes of illustration only, and that any L1 capsid protein coding sequence for any animal or human papillomavirus type can be used without deviating from the intended scope of the invention. Such HPV types include, without limitation, HPV types 16, 18, 31, 33, 35 (Gissman et al., *Cancer Cells*, 1987, vol. 5, p. 275, which disclosure is hereby incorporated by reference); and those HPV types disclosed in PCT publication no. WO 92/16636 to Boursnell et al., which disclosure is hereby incorporated by reference.

The preferred expression system used in the method of the invention is the baculovirus expression system, however, it is understood that any other expression system(s) can be employed herein provided the system(s) can expresses the L1 protein coding sequence. Examples of such systems include, without limitation, any prokaryotic and/or eukaryotic system(s) including adenoviruse, SV40, *E. coli*, Mar. 9, 1993CHO cells, vaccinia virus, insect viruses, yeast, bacteriophage virus or modified viruses, DNA plasmids, vectors and the like.

The host cell for expression of the L1 coding sequence is dependent on the expression system used. Examples of suitable host cells include, without limitaiton, bacteria (prokaryotic), microorganisms such as yeast, mammalian cells (eukaryotic) and insect cells. When using the baculovirus expression system, insect cells, such as Sf-9 or Sf-21 are preferred.

In another aspect of the invention, it was discovered that the L1 protein produces virus-like particles (VLPs), fragment(s), capsomer(s) or portion(s) thereof, formed from papillomavirus capsid protein. It has been discovered that the virus-like particle(s) comprises antigenic characteristic(s) similar to those of native infectious papillomavirus particles. More particularly, these VLPs contain an antigenic determinant that is specifically recognized by antibodies present in sera obtained from genital HPV-infected patients. For example, reaction of VLP-containing insect cell extracts with antisera directed against either denatured or non-denatured capsid epitopes, as deduced by immunoreactivities in Western blot and immunodotblot assays, suggested that conformational epitopes present in native HPV-11 infectious virions were also present on the baculovirus-produced HPV-11 VLPs of the present invention. Immunodotblot assays using human sera obtained from individuals with biopsy proven condylomata acuminatum correlated closely with results previously obtained in HPV-11 whole virus particle-based ELISA tests as described by Bonnez et al., Use of human papillomavirus type 11 virions in an ELISA to detect specific antibodies in humans with condylomata acuminata, 1991, *J. Gen. Virol.*, vol. 72, pp. 1343-1347, which disclosure is hereby incorporated by reference.

These morphologic and immunologic similarities to native HPV-11 virions suggest that recombinant VLPs produced in the baculovirus system will be useful in sero-epidemiology and pathogenesis studies of not only genital HPV infection but for any papillomavirus and for vaccine development. L1 has an intrinsic capacity for self-assembly. Thus, other papillomavirus proteins are not required for VLP formation in the baculovirus system. This supports the contention that VLPs to all types of papillomaviruses can be produced in accordance with the method described herein.

The VLPs of the invention can be used to raise antibodies, either in subjects for which protection against infection by HPV is desired, i.e., vaccines, or to heighten the immune response to an HPV infection already present. The VLPs of the invention can be injected into animal species to obtain antisera useful in diagnosis. In addition to polyclonal antisera, monoclonal antibodies can be obtained using the methods of Kohler and Milstein, or by modifications thereof, by immortalizing spleen or other antibody-producing cells from injected animals to obtain antibody-producing clones, i.e., hybridomas.

The antibodies obtained can be used for diagnosis of HPV infection in cervical biopsies or Papanicolaou smears and in assessing disease levels in humans or other subjects. In particular, diagnosis using the antibodies of the invention permits monitoring the evolution of the disease. The antibodies can be used in analysis of serum to detect the virus, as well as to monitor the progress of therapy with antiviral or other therapeutic agents directed to control of the infection or carcinoma. The antibodies can also be used as passive therapy, taking into account species variations.

The VLPs of the invention can be used in immunoassays to detect the presence of antibodies raised against HPV in the serum of patients suspected of harboring HPV infections or to titrate the sera of patients being treated with an anti-HPV vaccine.

The VLPs of the invention can be directly administered to a host to confer either protective immunity against HPV or, if the patient is already infected, to boost the patient's own immune response. For all applications, the VLPs are administered in immunogenic form. Optionally, the VLPs can be conjugated to an immunogenicity conferring carrier material, the material preferably being antigenically neutral. Depending on the use required, the VLPs of the invention have the ability to serve as type specific or broad range vaccines and diagnostics.

VLPs which are to be administered as vaccines can be formulated according to conventional and/or future methods for such administration to the subject to be protected and can be mixed with conventional adjuvants. The peptide expressed can be used as an immunogen in subunit vaccine formulations, which may be multivalent. The multivalent vaccine formulation can comprise VLPs each encoding a different L1 protein from different HPVs. The product may be purified for purposes of vaccine formulation from any vector/host systems that express the heterologous protein. The purified VLPs should be adjusted to an appropriate concentration, formulated with any suitable vaccine adjuvant and packaged for use. Suitable adjuvants include, but are not limited to: mineral gels, e.g., aluminum hydroxide; surface active substances such as lysolecithin, pluronic polyols; polyanions; peptides; oil emulsions; and potentially useful human adjuvants such as BCG (Bacille Calmette-Guerin) and *Comebacterium parvum*. The immunogen may also be incorporated into liposomes, or conjugated to polysaccharides and/or other polymers for use in a vaccine formulation. Many methods may be used to introduce the vaccine formulations described above; these include, but are not limited to, oral, intradermal, intramuscular, intraparitoneal, intravenous, subcutaneous and intranasal routes. If they are to be used directly, as diagnostic reagents, they are purified using conventional methods and packaged accordingly for such use. If they are to be used to produce antibodies for diagnostic purposes, convenient test animals can be used to prepare the appropriate antisera. Suitable hosts include mice, rats, rabbits, guinea pigs, or even larger mammals such as sheep. The antibodies can be used therapeutically so long as they are compatible with the host to be treated. Monoclonal antibodies having the proper species characteristics are preferred for this application.

The following Examples are provided to further illustrate the present invention.

EXAMPLE I

Materials and Methods

1. HPV-11 Viral DNA And pVL11L1 Baculovirus Transfer Vector Construction

HPV-11 genomic DNA was obtained from virus particles which were purified from experimentally induced athymic mouse xenografts as described by Rose et al., Expression of the full-length products of the HPV-6b and HPV-11 L2 open reading frames by recombinant baculovirus, and antigenic comparisons with HPV-11 whole virus particles, 1990, *J. Gen. Virol.*, vol. 71, pp. 2725-2729, which disclosure is hereby incorporated by reference. The L1 coding sequence was cloned by PCR amplification of purified genomic DNA, using primers designed to introduce BglII and EcoRI restriction enzyme sites at the 5' and 3' ends, respectively. The forward and reverse primer sequences, respectively, were, 5'-CGC AGA TCT ATG TDG CCT AGC-3' (SEQ. ID. NO. 1) and 5'-CAT ATG AAT TCC CAC AAC ACA CTG ACA CAC-3'(SEQ. ID. NO. 2). Restriction sites (underlined) were introduced proximal to the putative L1 start codon (bold text), and approximately 30 nucleotides downstream from the putative L1 stop codon, by primer-directed mutagenesis. Amplification was performed essentially as described by Bonnez et al., Antibody-mediated neutralization of human papillomavirus type 11 (HPV-11) infection in the nude mouse: Detection of HPV-11 mRNAs by the polymerase chain reaction, 1992, *J. Inf. Dis.*, vol. 165, pp. 376-380, which disclosure is hereby incorporated by reference, using 500 ng of each primer and 2 units of Taq DNA polymerase (Amplitaq, Perkin-Elmer Cetus Corp., Norwalk, Conn.). After amplification, the PCR product was digested with BglII and EcoRI. The 1539 base pair (bp) digestion product, which contained the entire HPV-11 L1 open reading frame (ORF), was purified by agarose gel electrophoresis as described by Rose et al., Expression of the full-length products of the HPV-6b and HPV-11 L2 open reading frames by recombinant baculovirus, and antigenic comparisons with HPV-11 whole virus particles, 1990, *J. Gen. Virol.*, vol. 71, pp. 2725-2729, which disclosure is hereby incorporated by reference, and cloned into the corresponding sites of a baculovirus transfer vector, pVL-1392 (M. D. Summers, Texas A&M University, College Station, Tex.). The resulting construct, pVL11L1, was used to co-transfect Sf-9 cells with *Autographa californica* nuclear polyhedrosis virus (AcNPV) genomic DNA according to the methods of Summers et al., A manual of methods for baculovirus vectors and insect cell culture procedures, 1987, Texas A&M University, College Station, T.X., which disclosure is hereby incorporated by reference. Recombinant baculoviruses were recovered by visual examination and selection of occlusion-negative (occ-) plaques, and were subjected to two further rounds of plaque-purification according to the methods of Summers et al., A manual of methods for baculovirus vectors and insect cell culture procedures, 1987, Texas A&M University, College Station, T.X., which disclosure is hereby incorporated by reference. Protein expression from isolated virus stocks was determined by Western blot.

2. SDS-PAGE And Western Blot Detection Of Recombinant L1 Expression In Sf-9 Cells Infected Sf-9 cell cultures were grown in 150 cm$^2$ tissue culture flasks and prepared for analytical SDS-PAGE and Western Blot assay. Non-recombinant or recombinant L1-infected cells were collected from flasks by resuspending with a pasteur pipet, and equal numbers of wild-type or recombinant L1-infected cells were centrifuged at 500×g for 10 minutes at 4° C. Supernatants were removed and cell pellets were transferred to ice, immediately resuspended in 1 ml lysis buffer (30 mM Tris, pH 7.6; 10 mM MgCl$_2$; 1 mM CaCl$_2$; 1 mM phenylmethylsulfonyl fluoride (PMSF); leupeptin (10 g/ml); 1% NP-40) and allowed to stand at room temperature for 15 minutes with periodic vortexing. After centrifugation at 500×g for 2 minutes at 4° C., the NP40-soluble fraction contained in the supernatant was removed and diluted 1:1 with 2× Laemmli sample buffer as described by Laemmli, Cleavage of structural proteins during the assembly of the head of the bacteriophage T4, 1970, *Nature*, vol. 277, pp. 680-685, which disclosure is hereby incorporated by reference, and heated to 95° C. for 3 minutes. The NP40-insoluble pellet (containing nuclear material) was washed once with cold PBS (1 mM PMSF: 10 g/ml leupeptin) and solubilized by boiling and vortexing in 1×Laemmli buffer. Samples were electrophoresed in 10% SDS polyacrylamide gels, followed by Coomassie-blue staining (FIG. 1, panel A) or blotting (FIG. 1, panel B) to an Immunobilon-P membrane (Millipore Corp., New Bedford, Mass.) as described by Rose et al., Expression of the full-length products of the HPV-6b and HPV-11 L2 open reading frames by recombinant baculovirus, and antigenic comparisons with HPV-11 whole virus particles, 1990, *J. Gen. Virol.*, vol. 71, pp. 2725-2729, which disclosure is hereby incorporated by reference.

3. Preparation Of Non-Recombinant And Recombinant L1 Stock Solutions

These assays were performed using dilutions of clarified (high-speed) supernatant stock solutions prepared from extracts of either AcNPV or Ac11L1-infected insect cells. Suspension cultures (100 ml) of Sf-9 cells infected either with AcNPV or Ac11L1 at an approximate multiplicity of infection of 10 plaque forming units per cell were incubated at 27° C. for 72 hours. Cultures were then centrifuged at 1,000×g for 10 minutes at 4° C. and cell pellets were resuspended in 20 ml homogenization buffer (lysis buffer with 1 M NaCl) and homogenized with 50 strokes in a Dounce homogenizer on ice. Homogenates were transferred to cold 30 ml screw-cap Corex tubes and centrifuged at 3,000×g for 10 minutes at 4° C. Low-speed supernatant fractions were then transferred to a clean tube and centrifuged at 100,000×g for 30 minutes at 4° C. Total protein concentrations of high speed supernatant fractions were measured by spectrophotometric absorption at 280 nm according to the procedure of Stoscheck, Quantitation of proteins, 1990, *Methods in Enzymology*, vol. 182, p. 54, Academic Press, Inc., New York, which disclosure is hereby incorporated by reference, and adjusted to equivalence with fresh homogenization buffer (protein concentrations approximately equal to 30 mg/ml). Glycerol was added to 10% (v/v) and stock solutions were aliquoted and stored at −20° C.

4. Western Blot And Immunodotblot Assays

Western blot and immunodotblot assays were used to determine linear and conformational epitope antibody specificities in rabbit antisera and human sera. The Western blot assays (FIG. 3, panel A, and FIG. 4) were performed using 2 l (about 60 g total protein) of recombinant L1 stock solution diluted 1:100 with 1×Laemmli sample buffer, which contains protein denaturation reagents as described by Laemmli, Cleavage of structural proteins during the assembly of the head of the bacteriophage T4, 1990, *Nature*, vol. 277, pp. 680-685, which disclosure is hereby incorporated by reference, and heated to 95° C. for 3 minutes. The denatured sample was loaded in a single 100 mm wide sample well, electrophoresed in a 10% SDS polyacrylamide gel, and blotted to an Immunobilon-P membrane.

Figure 3:
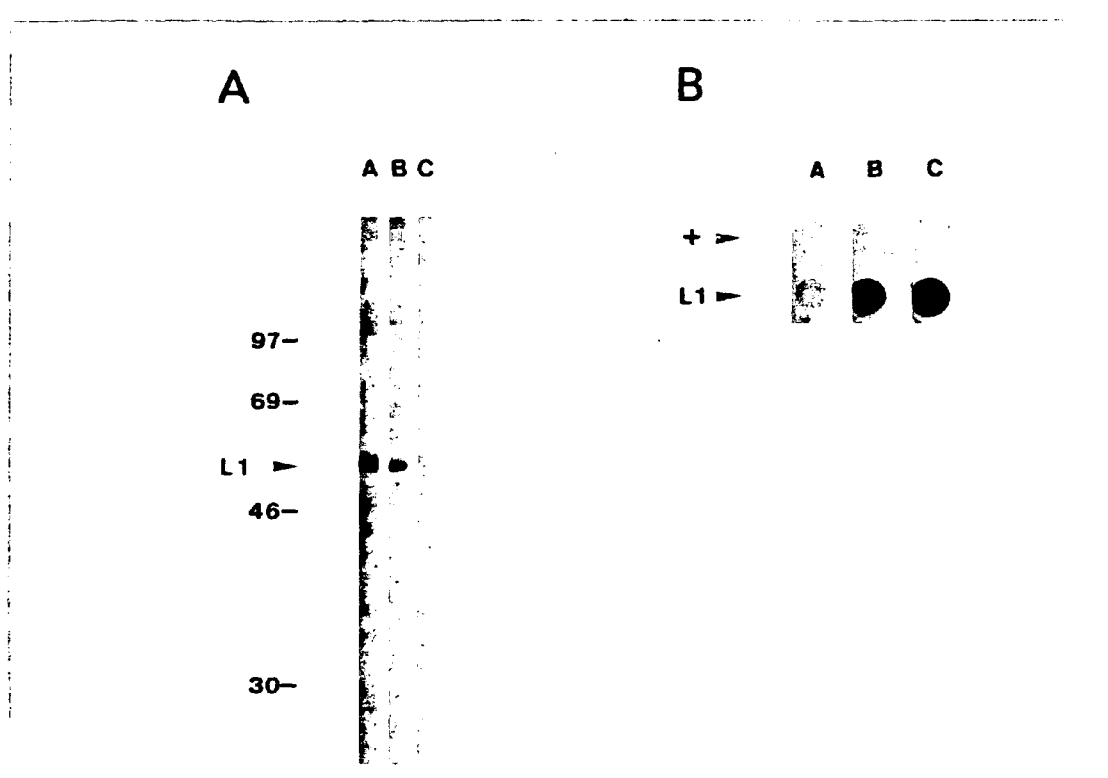
FIG. 3 shows Western blot and immunodotblot comparisons of rabbit antisera immunoreactivities with recombinant L1. In panel A, recombinant L1 insect cell lysate was Western blotted under denaturing conditions. In panel B, non-recombinant (+) or recombinant L1 (L1) insect cell lysates were applied to a blotting membrane under non-denaturing conditions. Strips A were probed with a rabbit polyclonal antiserum specific for the HPV L1 common epitope; strips B were probed with a rabbit polyclonal antiserum specific for the amino-terminal amino acid sequence of HPV L1; strips C were probed with a rabbit polyclonal whole virus particle antiserum.
Figure 4:
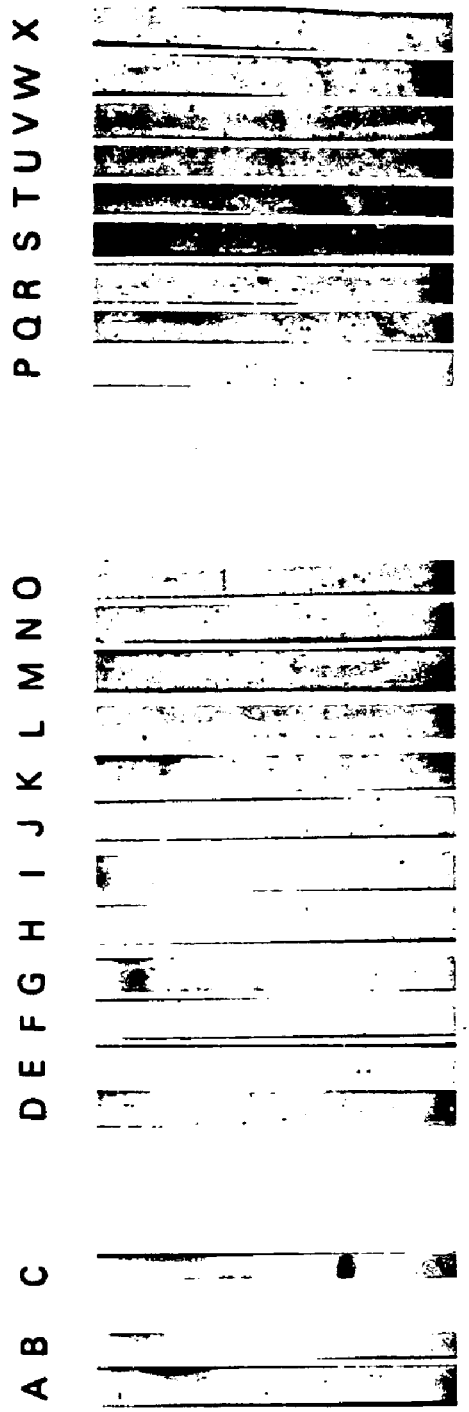
FIG. 4 shows a Western blot assay using recombinant L1 insect cell lysates. Strips A-X correspond to different primary antibodies used (strips A and B were reacted with pre- and post-immune rabbit anti-whole virus particle antisera, respectively; strip C was reacted with post-immune rabbit anti-denatured L1 common epitope antiserum; strips D-O were reacted with condyloma acuminatum patients' sera; strips P-X were reacted with control sera).

After blocking with a 2% BSA solution (Kirkegaard and Perry Labs, Inc., Gaithersburg, Md.) for 2 hours at 37° C., the membrane was sliced into 24, 4 mm wide strips, each containing about 2.5 g total protein. Thereafter, the strips were probed with antisera (FIG. 3, panel A, and FIG. 4).

For immunodotblot analysis, non-recombinant or recombinant L1 stock solutions were diluted 1:1,000 with cold PBS (1 mM $CaCl_2$) and 100 l aliquots (containing about 3.0 g total protein) were dotted onto an Immobilon-P membrane. Protein denaturation reagents were omitted from the immunodot blot sample preparation to preserve the native conformation of recombinant L1. Blocking, primary and secondary antibody diluent solutions, washes, and substrate used are as described by Strike et al., Expression in *Escherichia coli* of seven DNA segments comprising the complete L1 and L2 open reading frames of human papillomavirus type 6b and the location of the "common antigen", 1989, *J. Gen. Virol.*, vol. 70, pp. 543-555, which disclosure is hereby incorporated by reference. Primary antibody incubations were performed overnight at 4° C., second antibody incubations were done at room temperature for 90 minutes. For immunodotblots, all solutions except the substrate solution contained $CaCl_2$ at 1 mM. Primary antibody dilutions were 1:2,000 for rabbit antisera and 1:1,000 for human sera. Specifically-bound antibodies were detected with affinity-purified anti-rabbit (Kirkegaard and Perry Laboratories, Inc., Gaithersburg, Md.), or anti-human (TAGO Immunodiagnostics, Burlingame, Calif.) IgG-alkaline phosphatase conjugates used at dilutions of 1:2,000 and 1:5,000, respectively, using BCIP/NBT (Kirkegaard and Perry Laboratories, Inc.) as substrate. Immunodotblot reactions were assessed by visual comparison of non-recombinant and recombinant L1 dot intensities. A reaction was considered positive if the color intensity of the recombinant L1 dot was greater than the color intensity of the non-recombinant control dot present on the same strip.

5. Antisera

The denatured L1 antiserum used was described previously as anti-pEX480 by Strike et al., Expression in *Escherichia coli* of seven DNA segments comprising the complete L1 and L2 open reading frames of human papilloinavirus type 6b and the location of the "common antigen", 1989, *J. Gen. Virol.*, vol. 70, pp. 543-555, which disclosure is hereby incorporated by reference. This antiserum was obtained by rabbit immunization with a gel-purified bacterially-expressed fusion protein that contained a 160 amino acid sequence derived from the mid-region of the HPV-6b L1 open reading frame fused to the carboxy terminus of betagalactosidase, as described by Stanley et al., Construction of a new family of high efficiency bacterial expression vectors: Identification of cDNA clones coding for human liver proteins, 1984, *EMBO. J.*, vol. 3, pp. 1429-1434; and Strike et al., Expression in *Escherichia coli* of seven DNA segments comprising the complete L1 and L2 open reading frames of human papillomavirus type 6b and the location of the "common antigen", 1989, *J. Gen. Virol.*, vol. 70, pp. 543-555, which disclosures are hereby incorporated by reference. This sequence contains the papillomavirus L1 common antigen as described by Strike et al., Expression in *Escherichia coli* of seven DNA segments comprising the complete L1 and L2 open reading frames of human papillomavirus type 6b and the location of the "common antigen", 1989, *J. Gen. Viral.*, vol. 70, pp. 543-555 which disclosure is hereby incorporated by reference. The rabbit whole virus particle antiserum used was as described by Bonnez et al., Antibody-mediated neutralization of human papillomavirus type 11 (HPV-11) infection in the nude mouse: Detection of HPV-11 mRNAs by the polymerase chain reaction, 1992, *J. Inf. Dis.*, vol. 165, pp. 376-380, which disclosure is hereby incorporated by reference, and produced by immunization of rabbits with purified non-denatured HPV-11 virions, which were obtained from athymic mouse foreskin xenografts according to Bonnez et al., Antibody-mediated neutralization of human papillomavirus type 11 (HPV-11) infection in the nude mouse: Detection of HPV-11 mRNAs by the polymerase chain reaction, 1992, *J. Inf. Dis.*, vol. 165, pp. 376-380; and Kreider et al., Laboratory production in vivo of infectious human papillomavirus type 11, 1989, *J. Viral.*, vol. 61, pp. 590-593, which disclosures are hereby incorporated by reference. Patients' sera were obtained from individuals with biopsy-proven condyloma acuminatum. Serum specimens previously found positive by HPV-11 whole virus particle-based ELISA as described by Bonnez et al., Use of human papillomavirus type 11 virions in an ELISA to detect specific antibodies in humans with condylomata acuminata, 1991, *J. Gen. Viral.*, vol. 72, pp. 1343-1347, which disclosure is hereby incorporated by reference, were used to maximize the ability to detect antibodies directed against VLPs. Control sera were obtained from nuns who professed no lifetime sexual contact. These sera were negative for HPV-11 antibodies as determined by the HPV-11 particle-based ELISA as described by Bonnez et al., Use of human papillomavirus type 11 virions in an ELISA to detect specific antibodies in humans with condylomata acuminata, 1991, *J. Gen. Virol.*, vol. 72, pp. 1343-1347, which disclosure is hereby incorporated by reference.

6. Purification Of HPV-11 Virus-like Particles

Sf-9 cells (100 mL suspension culture) infected with the Ac11L1 recombinant baculovirus were pelleted, and the culture medium was centrifuged at 100,000×g at 4° C. for 1 hour. The pelleted material was resuspended in 1 ml of buffer A (Phosphate-buffered saline (PBS); 1M NaCl; 1 mM $CaCl_2$; 1 mM $MgCl_2$; 1 mM phenylmethylsulfonyl fluoride; 10 g/mL Leupeptin) and applied to a 20-60% sucrose step gradient. After centrifugation at 150,000×g at 4° C. for 20 hours, the lower band (visualized at the 50-60% sucrose interface) was removed with a pasteur pipet. The recovered band was diluted 1:10 in buffer A and pelleted at 150,000×g for 1 hour. The pelleted material, upon examination by electron microscopy, was predominantly composed of HPV-11 VLPs (FIG. 2).

7. Electron Microscopy of VLPs

Figure 2:
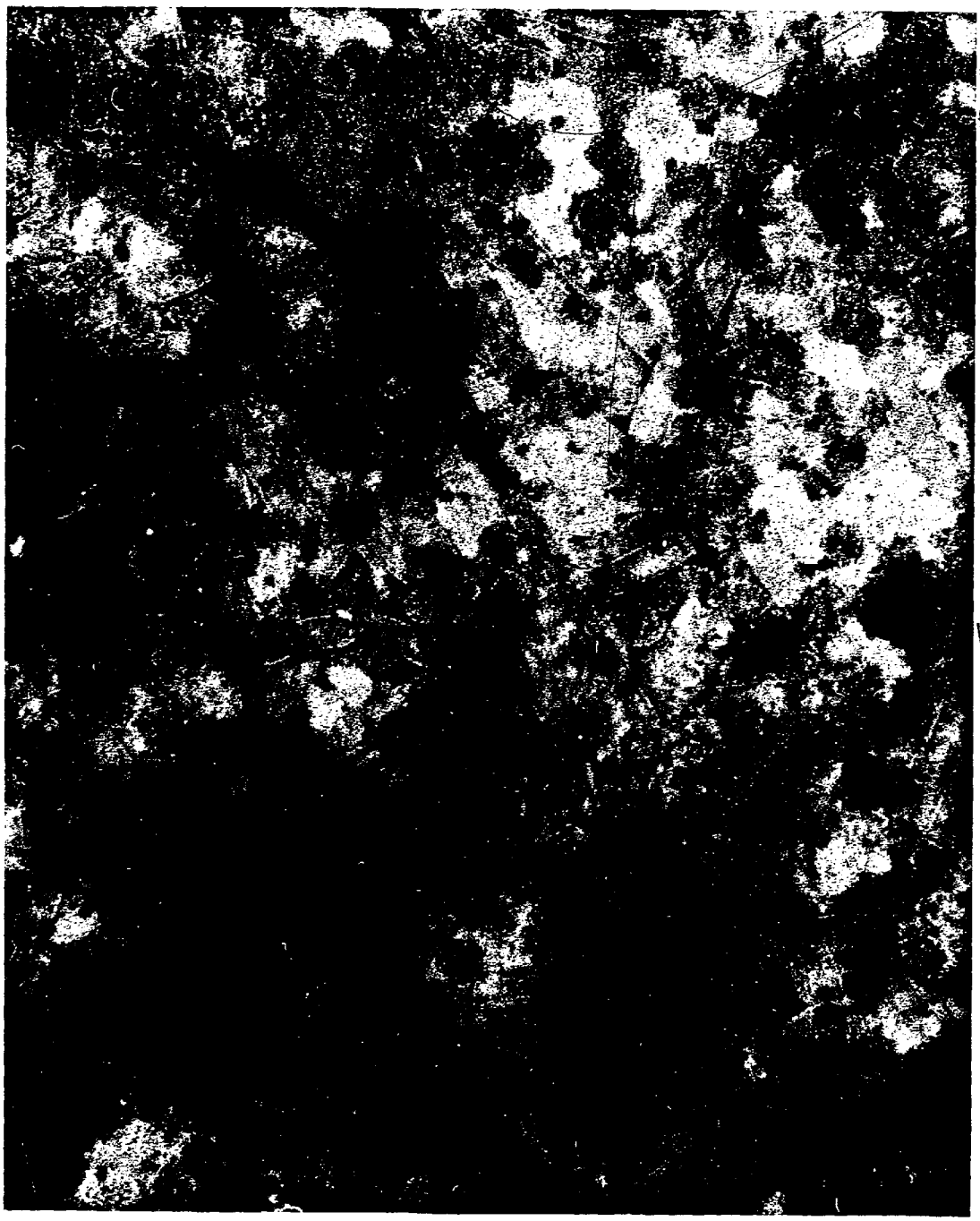
FIG. 2 shows an electron micrograph of HPV-11 virus-like particles recovered by sucrose density centrifugation from Ac11L1-infected Sf-9 cells. The VLPs shown are approximately 52 nm in diameter (scaled by magnification standards) and possess icosahedral symmetry, consistent with published observations regarding the morphologic characteristics of naturally-occurring papillomavirions.
Figure 6:
FIG. 6 is an electron micrograph of HPV type 6 VLPs, produced by the construction and expression of an HPV-6 L1 recombinant baculovirus (Ac6L1).
Figure 7:
FIG. 7 is an electron micrograph of HPV type 16 VLPs, produced by the construction and expression of an HPV-16 L1 recombinant baculovirus (Ac16L1).

VLPs purified by sucrose density gradient centrifugation were identified by electron microscopy after staining with 2% neutral buffered phosphotungstic acid (FIGS. 2, 6, and 7).

EXAMPLE II

Expression And Immunologic Detection Of Recombinant HPV-11 L1 Protein In Sf-9 cells SDS-PAGE analysis of total Sf-9 cell proteins from insect cells infected with the recombinant virus Ac11L1 demonstrated a novel 55 kD protein seen by Coomassie-blue staining in Ac11L1-infected cells (FIG. 1A, lane 3). With reference to FIGS. 1 (A and B), FIG. 1A shows Coomassie-stained SDS polyacrylamide gel of wild-type AcNPV and recombinant Ac11L1-infected Sf-9 cell lysates and FIG. 1B shows Western blot of wild-type AcNPV and recombinant Ac11L1-infected Sf-9 cell lysates probed with a rabbit polyclonal antiserum specific for the HPV L1 common epitope. Non-recombinant (lanes 1,2) and recombinant L1-infected (lanes 3,4) Sf-9 cell lysates were fractionated into insoluble (lanes 1,3) and soluble (lanes 2,4) fractions, and electrophoresed on 10% polyacrylamide gels. Molecular reference ($M_r$) markers are displayed at the left, and the arrow at the right indicates the approximate position of recombinant L1 (about 55 kD $M_r$). This protein is not present in wild-type AcNPV lysates, and co-migrates with a protein that is immunoreactive (FIG. 1B, lanes 3 and 4) with a rabbit antiserum prepared against the linear HPV L1 common antigen as described by Strike et al., Expression in *Escherichia coli* of seven DNA segments comprising the complete L1 and L2 open reading frames of human papillomavirus type 6b and the location of the "common antigen", 1989, *J. Gen. Viral.*, vol. 70, pp. 543-555, which disclosure is hereby incorporated by reference. Lower $M_r$ L1-immunoreactive bands were also detected and may be derived from degradation of the full-length L1 product (FIG. 1B, lanes 3 and 4). Although the predominant portion of L1 produced in this system appeared in the NP40-insoluble fraction, approximately 25-30% was present in the NP40-soluble fraction (FIG. 1B, lane 4). Maximal L1 accumulation occurred at 72 hours post-infection.

EXAMPLE III

Electron Microscopic Visualization of VLPs

Electron micrographs of negatively stained preparations of sucrose banded VLPs (FIGS. 2, 6, and 7) showed distinct VLPs. FIG. 2 shows HPV-11 capsid-like particles which were present at the 50-60% interface of the sucrose density gradient. FIG. 6 shows HPV type 6b (HPV-6b) capsid-like particles which resulted from the expression of the HPV-6b L1 coding sequence in the baculovirus system, and which were purified in exactly the same manner. FIG. 7 demonstrates that this method is also suitable for the production of HPV type 16 (HPV-16) VLPs, upon expression of the HPV-16 L1 coding sequence. Particle diameters determined by direct measurement of the VLPs in FIG. 2, were approximately 52 nm. This measurement is consistent with the diameter of isolated papillomavirus virions as described by Klug et al., Structure of viruses of the papilloma-polyoma type I: Human wart virus, 1965, *J. Mol. Biol.*, vol. 11, pp. 403-423, which disclosure is hereby incorporated by reference.

EXAMPLE IV

Immunoreactivity Of HPV-11 VLP-Containing Insect Cell Extracts With Rabbit Antisera The immunologic properties of the recombinant L1 protein were studied using rabbit antisera that reacted with native or denatured L1 protein epitopes. Rabbit antiserum pEX480, directed against the common papillomavirus antigen, reacted well with denatured recombinant L1 in Western blot assays, but did not react with the same antigen preparation by immunodotblot, a type of immunoassay in which the antigen is placed on the blotting membrane under non-denaturing conditions (FIG. 3, compare strips A). In contrast to the pattern of reactivity exhibited by anti-pEX480, the rabbit polyclonal antiserum raised against HPV-11 whole virus particles did not react with recombinant L1 by Western blot, but reacted strongly with recombinant L1 in the immunodotblot assay (FIG. 3, compare strips C). This reactivity was specific as demonstrated by lack of reactivity in the post-immune serum against the native non-recombinant control preparation (FIG. 3, panel B, strip C). Rabbit antiserum pEX215 was included in these immunoassays to allow comparison of the relative amounts of L1 present in the two types of immunoassays. The level of immunoreactivity of the pEX215 antiserum with recombinant L1 in both formats is roughly equivalent (FIG. 3, strips B), indicating that the amounts of L1 present are approximately equal. Furthermore, the observation that this antiserum is able to react with L1 in both formats suggests that the linear immunoreactive L1 amino-terminal epitope(s) recognized by the pEX215 antiserum is not obscured by the adoption of higher-order L1 conformation.

EXAMPLE V

Immunoreactivity Of VLP-Containing Insect Cell Extracts With Human Sera

Figure 5:
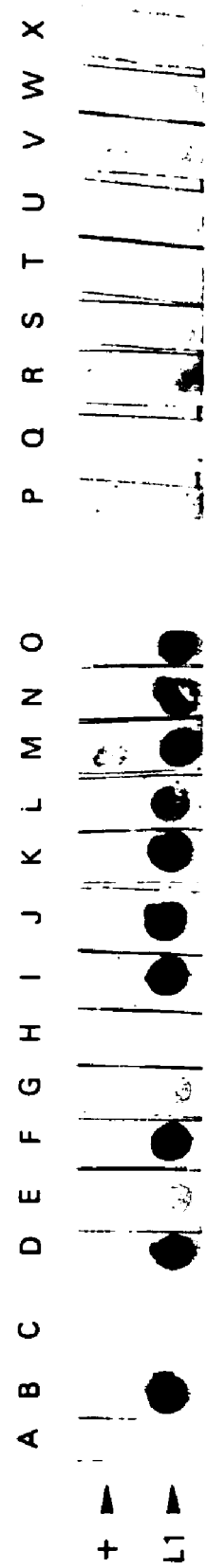
FIG. 5 shows an immunodotblot assay using insect cell lysates. The letters above the strips correspond to different primary antibodies used, which were the same as described in FIG. 4.

To determine the prevalence of antibodies in human sera directed against linear versus conformational epitopes, sera obtained from individuals with biopsy-proven condyloma acuminatum were evaluated in Western blot and immunodotblot assays using VLPs as antigen. None of the patients' or control sera were immunoreactive with denatured recombinant L1 by Western blot (FIG. 4, strips D-O (patients) and P-X (controls)). Conversely, 11 of 12 patients' sera (FIG. 5, strips D-O were read as positive, with the exception of strip H) and 0 of 9 control sera (FIG. 5, strips P-X) were immunoreactive with recombinant L1 by immunodotblot, a highly statistically significant difference ($p=7\times10^{-5}$; Fisher's exact test). This result correlates well with results previously obtained using the same sera in an HPV-11 particle-based ELISA as described by Bonnez et al., Use of human papillomavirus type 11 virions in an ELISA to detect specific antibodies in humans with condylomata acuminata, 1991, *J. Gen. Viral.*, vol. 72, pp. 1343-1347, which disclosure is hereby incorporated by reference.

RESULTS

Immunologic observations suggest that recombinant L1 adopts a native conformation. The rabbit antiserum raised against the denatured L1 common antigen was immunoreactive only with denatured recombinant L1 (i.e., by Western blot), whereas the rabbit antiserum raised against non-denatured whole virus particles reacted only with non-denatured recombinant L1 (i.e., by immunodotblot). Furthermore, human sera from condyloma acuminatum patients which were reactive with HPV-11 virions in an ELISA according to Bonnez et al., Use of human papillomavirus type 11 virions in an ELISA to detect specific antibodies in humans with condylomata acuminata, 1991, *J. Gen. Viral.*, vol. 72, pp. 1343-1347, also reacted with non-denatured HPV-11 recombinant L1. Therefore, it appears that the conformational epitopes of the VLPs of the invention are similar to those present in native HPV-11 virions, which are recognized by the human immune system during natural infection. Several studies of papillomavirus serology demonstrate that conformational epitope antibody specificities are good indicators of papillomavirus infection (Bonnez et al., Use of human papillomavirus type 11 virions in an ELISA to detect specific antibodies in humans with condylomata acuminata, 1991, *J. Gen. Virol.*, vol. 72, pp. 1343-1347; Bonnez et al., Evolution of the antibody response to human papillomavirus type 11 (HPV-11) in patients with condyloma acuminatum according to treatment response, 1991, *J. Med. Virol.*, 1991, in press; Bonnez et al., Antibody-mediated neutralization of human papillomavirus type 11 (HPV-11) infection in the nude mouse: Detection of HPV-11 mRNAs by the polymerase chain reaction, 1992, *J. Inf. Dis.*, vol. 165, pp. 376-380; Christensen et al., Detection of human serum antibodies that neutralize infectious human papillomavirus type 11 virions, 1992, *J. Gen. Virol.*, vol. 73, pp. 1261-1267; Kienzler et al., Humoral and cell-mediated immunity to human papillomavirus type 1 (HPV-1) in human warts, 1983, *Br. J. Dermatol.*, vol. 108, pp. 665-672; and Steele et al., Humoral assays of human sera to disrupted and nondisrupted epitopes of human papillomavirus type 1, 1990, *Virology*, vol. 174, pp. 388-398, which disclosures are hereby incorporated by reference). These specificities can also play a significant role in viral pathogenesis. For instance, a rabbit antiserum directed against whole HPV-11 particles neutralizes HPV-11 infectivity (Bonnez et al., Antibody-mediated neutralization of human papillomavirus type 11 (HPV-11) infection in the nude mouse: Detection of HPV-11 mRNAs by the polymerase chain reaction, 1992, *J. Inf. Dis.*, vol. 165, pp. 376-380; and Christensen et al., Antibody-mediated neutralization in vivo of infectious papillomavirus, 1990, J. Virol., vol. 64, pp. 3151-3156). Furthermore, Christensen et al., Detection of human serum antibodies that neutralize infectious human papillomavirus type 11 virions, 1992, J. Gen. Virol., vol. 73, pp. 1261-1267, using human sera reported a correlation between anti-whole HPV-11 virion antibody and serum neutralizing activity. Detection of such antibodies with the recombinant L1 VLPs of the present invention can have diagnostic and functional significance.

When taking into account construction of the recombinant baculovirus, some of the early recombinant baculoviruses we constructed had the correct L1 coding sequence, but were not producing detectable levels of L1 proteins. This caused us to look at the 3' untranslated regions of the HPV-11 and several other HPV L1 coding sequences. It was determined that a pentanucleotide mRNA degradation signal sequence, AUUUA, (Shaw G. and Kamen R., A conserved AU sequence from the 3' untranslated region of GM-CSF mRNA mediates selective mRNA degradation, *Cell,* 1986, vol. 46, pp. 659-67; Cole M D. and Mango S E., cis-acting determinants of c-myc mRNA stability, 1990, *Enzyme*, vol. 44, pp. 167-80; Shyu A B et al., Two distinct destabilizing elements in the c-fos message trigger deadenylation as a first step in rapid mRNA decay, *Genes & Development,* 1991, vol. 5, pp. 221-31; Savant-Bhonsale S, and Cleveland D W., Evidence for instability of mRNAs containing AUUUA motifs mediated through translation-dependent assembly of a: 20S degradation complex, *Genes & Development,* 1992, vol. 6, pp. 1927-37, which disclosures are hereby incorporated by reference) was within 30 nucleotides of the stop codon of the HPV-11 L1 coding sequence, and in addition, the other HPV types looked at had the AUUUA sequence in the vicinity of the L1 stop codon as well. If this sequence were removed, or a mutation introduced, that the expression level of the L1 protein could be increased. Therefore, PCR primers to amplify the L1 coding sequence from HPV-11 genomic DNA which not only incorporated restriction enzyme sites for cloning, but also mutated the AUUUA pentanucleotide sequence 30 nucleotides downstream from the L1 stop codon as well were designed. Scaleup of this clone produced extremely high levels of L1 protein. Reports using the BEVS system have given levels of recombinant protein production in the range of 300-500 mg/liter of cell culture. In the present invention, levels for recombinant L1 protein production were much greater, about 600-800 mg/liter, possibly due to the removal of the L1 degradation signal sequence in the 3' untranslated region.

The present invention has been described in some detail by way of illustration and example for purposes of clarity of understanding, however, it will be obvious that certain changes and modifications may be practiced within the scope of the appended claims.

We claim:

1. A purified, non-infectious, human papillomavirus type 16 L1 virus-like particle or capsomere, wherein said virus-like particle or capsomere is conformationally correct.

2. The purified, non-infectious, human papillomavirus type 16 L1 virus-like particle or capsomere according to claim 1, wherein the virus-like particle or capsomere is produced from the expression of the HPV-16 L1 capsid protein coding sequence, said capsid protein comprising HPV-16 L1 capsid protein.

3. The purified, non-infectious, human papillomavirus type 16 L1 virus-like particle or capsomere according to claim 1, wherein the particle or capsomere is recognized by antibodies present in sera obtained from HPV-16 infected human patients.

4. A method of producing antibodies against human papillomavirus type 16 in a subject, said method comprising administering to the subject an effective amount of a purified, non-infectious human papillomavirus virus-like particle or capsomere according to claim 1 under conditions effective to induce production of antibodies against human papillomavirus type 16 in the subject.

5. The method according to claim 4, wherein the subject is infected with human papillomavirus type 16.

6. A method of treating or preventing human papillomavirus type 16 infection in a human patient, said method comprising administering to a human patient an effective amount of a purified, non-infectious human papillomavirus virus-like particle or capsomere according to claim 1 under conditions effective to neutralize human papillomavirus type 16 virions, thereby treating or preventing human papillomavirus type 16 infection in the patient.

7. An isolated non-infectious human papillomavirus type 16 L1 virus-like particle or capsomere, wherein the virus-like particle or capsomere is conformationally correct.

8. The isolated non-infectious human papillomavirus type 16 L1 virus-like particle or capsomere according to claim 7, wherein said virus-like particle or capsomere induces in mammals formation of antibodies that neutralize infectious HPV-16 virions.

9. The isolated non-infectious human papillomavirus type 16 L1 virus-like particle according to claim 7, wherein the virus-like particle has a size equal to the size of HPV-16 virions.

10. The isolated non-infectious human papillomavirus type 16 L1 virus-like particle according to claim 9, wherein the virus-like particle has a diameter of 50-55 nm.

11. The isolated non-infectious human papillomavirus type 16 L1 virus-like particle or capsomere according to claim 7, wherein the virus-like particle or capsomere is recognized by antibodies present in sera obtained from HPV-16 infected human patients.

12. The isolated non-infectious human papillomavirus type 16 L1 virus-like particle according to claim 7.

13. The isolated non-infectious human papillomavirus type 16 L1 capsomere according to claim 7.

14. The isolated non-infectious human papillomavirus type 16 L1 virus-like particle or capsomere according to claim 7, wherein the virus-like particle or capsomere is produced from the expression of the HPV-16 L1 capsid protein coding sequence, said capsid protein comprising HPV-16 L1 capsid protein.

15. A method of producing antibodies against human papillomavirus type 16 in a subject, said method comprising administering to the subject an effective amount of the isolated non-infectious human papillomavirus virus-like particle or capsomere according to claim 7 under conditions effective to induce production of antibodies against human papillomavirus type 16 in the subject.

16. The method according to claim 15, wherein the subject is infected with human papillomavirus type 16.

17. A method of treating or preventing human papillomavirus type 16 infection in a human patient, said method comprising administering to a human patient an effective amount of the isolated non-infectious human papillomavirus virus-like particle or capsomere according to claim 7 under conditions effective to neutralize human papillomavirus type 16 virions, thereby treating or preventing human papillomavirus type 16 infection in the patient.

18. An isolated non-infectious, human papillomavirus virus-like particle or capsomere produced according to the method comprising:
    infecting a cell with a recombinant expression vector containing a human papillomavirus type-16 L1 capsid protein coding sequence, under conditions facilitating expression of L1 capsid protein, thereby producing a non-infectious human papillomavirus virus-like particle or capsomere, wherein the particle or capsomere is conformationally correct and
    isolating said virus-like particle or capsomere.

19. The isolated non-infectious, human papillomavirus virus-like particle or capsomere according to claim 18, wherein the virus-like particle or capsomere is recognized by antibodies present in sera obtained from HPV-16 infected human patients.

20. An isolated non-infectious, human papillomavirus virus-like particle according to claim 18.

21. An isolated non-infectious, human papillomavirus capsomere according to claim 18.

22. A human papillomavirus type-16 vaccine comprising:
    the isolated non-infectious human papillomavirus type 16 L1 virus-like particle or capsomere according to claim 7 and
    one or more adjuvants.

23. The human papillomavirus type-16 vaccine according to claim 22 further comprising:
    one or more human papillomavirus virus-like particles or capsomeres each comprising an L1 capsid protein from a human papillomavirus type other than HPV-16.

24. An isolated non-infectious human papillomavirus type 16 virus-like particle or capsomere consisting of HPV-16 L1, wherein the virus-like particle or capsomere is conformationally correct.

25. An isolated non-infectious human papillomavirus type 16 L1 virus-like particle or capsomere according to claim 24, wherein the virus-like particle or capsomere is produced from the expression of the HPV-16 L1 capsid protein coding sequence, said capsid protein consisting of HPV-16 L1 capsid protein.

26. A purified, non-infectious, human papillomavirus type 16 L1 virus-like particle or capsomere consisting of L1 capsid protein, wherein the virus-like particle or capsomere is conformationally correct and is produced from the expression of the HPV-16 L1 capsid protein coding sequence alone.

27. A method of producing antibodies against human papillomavirus type 16 in a subject, said method comprising administering to the subject an effective amount of an isolated non-infectious human papillomavirus type 16 virus-like particle or capsomere according to claim 24 under conditions effective to induce production of antibodies against human papillomavirus type 16 in the subject.

28. The method according to claim 27, wherein the subject is infected with human papillomavirus type 16.

29. A method of treating or preventing human papillomavirus type 16 infection in a human patient, said method comprising administering to a human patient an effective amount of an isolated non-infectious human papillomavirus type 16 virus-like particle or capsomere according to claim 24 under conditions effective to neutralize human papillomavirus type 16 virions, thereby treating or preventing human papillomavirus type 16 infection in the patient.

30. A human papillomavirus type-16 vaccine comprising:
    an isolated non-infectious human papillomavirus type 16 virus-like particle or capsomere according to claim 24 and
    one or more adjuvants.

31. The human papillomavirus type-16 vaccine according to claim 30 further comprising:
    one or more human papillomavirus virus-like particles or capsomeres each comprising an L1 capsid protein from a human papillomavirus type other than HPV-16.

32. A method of producing antibodies against human papillomavirus type 16 in a subject, said method comprising administering to the subject an effective amount of a purified, non-infectious, human papillomavirus type 16 L1 virus-like particle or capsomere according to claim 26 under conditions effective to induce production of antibodies against human papillomavirus type 16 in the subject.

33. The method according to claim 32, wherein the subject is infected with human papillomavirus type 16.

34. A method of treating or preventing human papillomavirus type 16 infection in a human patient, said method comprising administering to a human patient an effective amount of a purified, non-infectious, human papillomavirus type 16 L1 virus-like particle or capsomere according to claim 26 under conditions effective to neutralize human papillomavirus type 16 virions, thereby treating or preventing human papillomavirus type 16 infection in the patient.

35. A human papillomavirus type-16 vaccine comprising:
    a purified, non-infectious, human papillomavirus type 16 L1 virus-like particle or capsomere according to claim 26 and
    one or more adjuvants.

36. The human papillomavirus type-16 vaccine according to claim 35 further comprising:
    one or more human papillomavirus virus-like particles or capsomeres each comprising an L1 capsid protein from a human papillomavirus type other than HPV-16.

37. A method of producing antibodies against human papillomavirus type 16 in a subject, said method comprising administering to the subject an effective amount of an isolated non-infectious human papillomavirus type 16 L1 virus-like particle according to claim 25 under conditions effective to induce production of antibodies against human papillomavirus type 16 in the subject.

38. The method according to claim 37, wherein the subject is infected with human papillomavirus type 16.

39. A method of treating or preventing human papillomavirus type 16 infection in a human patient, said method comprising administering to a human patient an effective amount of an isolated non-infectious human papillomavirus type 16 L1 virus-like particle according to claim 25 under conditions effective to neutralize human papillomavirus type 16 virions, thereby treating or preventing human papillomavirus type 16 infection in the patient.

40. A human papillomavirus type-16 vaccine comprising:
    an isolated non-infectious human papillomavirus type 16 L1 virus-like particle according to claim 25 and
    one or more adjuvants.

41. The human papillomavirus type-16 vaccine according to claim 40 further comprising:

one or more human papillomavirus virus-like particles or capsomeres each comprising an L1 capsid protein from a human papillomavirus type other than HPV-16.

42. An isolated non-infectious human papillomavirus type 16 virus-like particle or capsomere comprising HPV-16 L1, wherein the virus-like particle or capsomere is conformationally correct.

43. The isolated non-infectious, human papillomavirus type 16 L1 virus-like particle or capsomere according to claim 42, wherein said L1 is expressed in a cell using a recombinant baculovirus expression system.

44. The isolated non-infectious, human papillomavirus type 16 L1 virus-like particle or capsomere according to claim 43, wherein said recombinant baculovirus expression system is produced by co-transfecting a cell with a baculovirus transfer vector comprising a papillomavirus HPV-16 L1 capsid protein coding sequence and *Autographa californica* nuclear polyhedrosis virus genomic DNA, and thereafter recovering recombinant baculoviruses.

* * * * *